United States Patent
Kruecker et al.

(10) Patent No.: US 9,651,662 B2
(45) Date of Patent: May 16, 2017

(54) INTERVENTIONAL NAVIGATION USING 3D CONTRAST-ENHANCED ULTRASOUND

(75) Inventors: Jochen Kruecker, Washington, DC (US); Sheng Xu, Rockville, MD (US); Hui Jiang, Issaquah, WA (US)

(73) Assignee: Koninklijke Philips N.V., Eindhoven (NL)

( * ) Notice: Subject to any disclaimer, the term of this patent is extended or adjusted under 35 U.S.C. 154(b) by 877 days.

(21) Appl. No.: 12/742,255

(22) PCT Filed: Nov. 13, 2008

(86) PCT No.: PCT/IB2008/054769
§ 371 (c)(1),
(2), (4) Date: May 11, 2010

(87) PCT Pub. No.: WO2009/063423
PCT Pub. Date: May 22, 2009

(65) Prior Publication Data
US 2010/0268085 A1     Oct. 21, 2010

Related U.S. Application Data (60) Provisional application No. 61/052,288, filed on May 12, 2008, provisional application No. 60/988,472, filed on Nov. 16, 2007.

(51) Int. Cl.
*G01S 15/89* (2006.01)
*A61B 8/08* (2006.01)
(Continued)

(52) U.S. Cl.
CPC .......... *G01S 15/899* (2013.01); *A61B 8/0833* (2013.01); *A61B 8/4245* (2013.01);
(Continued)

(58) Field of Classification Search
CPC .......... A61B 8/463; A61B 8/481; A61B 8/483
(Continued)

(56) References Cited

U.S. PATENT DOCUMENTS 6,014,473 A * 1/2000 Hossack et al. ............. 382/294
2002/0072677 A1* 6/2002 Sevick-Muraca et al. ... 600/473
(Continued)

FOREIGN PATENT DOCUMENTS

| EP | 1795130 A1 | 6/2007 |
|----|------------|--------|
| EP | 1857834 A2 | 11/2007 |

(Continued)

OTHER PUBLICATIONS

Rygh et al, Intraoperative navigated 3-dimensional ultrasound angiography in tumor surgery, 2006, Elsevier, Surgical Neurology 66 (2006), 581-592.*

(Continued)

*Primary Examiner* — Rochelle Turchen (57) ABSTRACT

A method for interventional navigation using 3D contrast-enhanced ultrasound (CEUS) imaging includes acquiring a reference 3D CEUS volume and tracking information during a useful lifetime of a contrast enhancement agent administered to the anatomy. Real-time tracked tissue images are acquired during the interventional procedure. In addition, a corresponding CEUS multiplanar reconstruction (MPR) for at least one of the acquired real-time tracked tissue images is generated. At least one of the acquired real-time tracked tissue images is displayed along with the corresponding CEUS MPR. The displayed real-time tracked tissue image includes at least an image of the instrument within the desired portion of the anatomy and the CEUS MPR corresponds to the displayed real-time tracked tissue image. Thus, the contrast enhanced image information and tissue image information are concurrently display for the interventional (Continued)

navigation at least subsequent to the expiration of the contrast enhancement useful lifetime.

19 Claims, 3 Drawing Sheets

(51) Int. Cl.
 *G01S 7/52* (2006.01)
 *A61B 8/00* (2006.01)
(52) U.S. Cl.
 CPC ........ *A61B 8/4263* (2013.01); *G01S 7/52074* (2013.01); *G01S 7/52098* (2013.01); *G01S 15/8993* (2013.01)
(58) Field of Classification Search
 USPC ........................................ 600/437, 458, 462
 See application file for complete search history.

(56) References Cited

U.S. PATENT DOCUMENTS

| | | | |
|---|---|---|---|
| 2003/0231789 A1 | 12/2003 | Willis et al. | |
| 2004/0193053 A1* | 9/2004 | Kato | 600/440 |
| 2004/0267128 A1* | 12/2004 | Matsumura | 600/458 |
| 2005/0033176 A1* | 2/2005 | Kawabata et al. | 600/454 |
| 2006/0020204 A1 | 1/2006 | Serra et al. | |
| 2006/0239585 A1 | 10/2006 | Valadez et al. | |
| 2007/0167801 A1 | 7/2007 | Webler et al. | |
| 2008/0177138 A1* | 7/2008 | Courtney et al. | 600/109 |
| 2008/0275335 A1* | 11/2008 | Zhang et al. | 600/424 |
| 2009/0124907 A1* | 5/2009 | Bruce et al. | 600/458 |

FOREIGN PATENT DOCUMENTS

| | | |
|---|---|---|
| JP | 2007125169 A | 5/2007 |
| RU | 2173539 C2 | 9/2001 |
| WO | WO9625881 A | 8/1996 |
| WO | 9729682 A1 | 8/1997 |
| WO | WO2007067323 A2 | 6/2007 |

OTHER PUBLICATIONS

Edward A. Gardner et al., "Removing Local Motion From Ultrasonic Images Using Nonaffine Registration for Contrast Quantification," IEEE Int'l Ultrasonics, Ferroelectrics, and Frequency Control Conf., pp. 1718-1721, 2004.

M. Krix, "Quantification of perfusion of liver tissue and metastases using a multivessel model for replenishment kinetics of ultrasound contrast agents," Ultrasound in medicine & biology, vol. 30, pp. 1355-1363, 2004.

J. Kruecker, S. Xu, N. Glossop, Z. Neeman, J. Locklin, and B. J. Wood, "Electromagnetic needle tracking and multi-modality imaging for biopsy and ablation guidance," in Int J CARS, Berlin, Germany, 2007, pp. 147-150.

S. Xu et al., "Real-time Motion Tracking Using 3D Ultrasound," Proc. SPIE vol. 6509, 65090X (Mar. 21, 2007).

S. Xu et al., "Closed-loop control in fused MR-TRUS image-guided prostrate biopsy," MICCAI 2007, 10th Int Conference on Medical Image Computing Assisted Intervention (Jun. 19, 2007).

A Fenster et al., "The Use of Three-Dimensional Ultrasound Imaging in Breast Biopsy and Prostate Therapy", Measurement, Institute of Measurement and Control, London, GB, vol. 36, No. 304, Oct. 1, 2004, pp. 245-256.

Moriyasu et al., "1009", Ultrasound in Medicine and Biology, New York, NY, US, vol. 32, No. 5, May 1, 2006, p. P4.

E.B. Levy et al., "Electromagnetic Tracking-Guided Percutaneous Intrahepatic Portosystemic Shunt Creation in a Swine Model", J. Vasc. and Intervent. Radiology, 18:pp. 303-307, 2007.

\* cited by examiner

INTERVENTIONAL NAVIGATION USING 3D CONTRAST-ENHANCED ULTRASOUND

CROSS REFERENCE TO RELATED CASES

Applicants claim the benefit of International Application Number PCT/IB2008/054769, filed Nov. 13, 2008, and Provisional Application Ser. No. 60/988,472, filed Nov. 16, 2007, and Provisional Application Ser. No. 61/052,288, filed May 12, 2008.

This invention was made in the performance of a Cooperative Research and Development Agreement with the United States Public Health Service (CRADA No. NCI-NIHCC-01864). The Government of the United States may have certain rights in the invention.

The present embodiments relate generally to ultrasound diagnostic imaging systems and more particularly, to a method and apparatus for interventional navigation using 3D contrast enhanced ultrasound (CEUS).

Ultrasound imaging is one of the primary image guidance methods for many minimally invasive and interventional procedures. In particular, most needle biopsies and needle-based ablation procedures are guided by ultrasound. The advantages of ultrasound include the real time imaging capability, low cost, flexibility in its application, and the fact that no ionizing radiation is used. However, non-enhanced ultrasound, including the commonly used gray-scale ultrasound image, may not be able to visualize a particular target (e.g., a tumor) with the desired contrast, and in some cases, may not visualize the target at all. In those cases, needle placement becomes very difficult and prone to inaccuracies, since it involves imaging the target using a different modality, and "mentally" transferring the tumor location into the real time ultrasound image based on anatomical landmarks near the tumor identified in both imaging modalities. The result may be false-negative biopsies, failed tumor therapy, and in general, poor therapeutic outcomes.

Contrast enhanced ultrasound (CEUS) imaging is another form of ultrasound imaging that refers to ultrasound imaging after intra-venous injection of an ultrasound contrast agent (such as Definity®, Bristol-Myers Squibb). On modern ultrasound scanners, specific imaging modes have been implemented to take advantage of the non-linear acoustic response of contrast agents, thus only highlighting tissue with contrast uptake. The resulting image is called "contrast image" and has a very different appearance compared to non-contrast images. It is also possible to image tissue after contrast injection in regular grayscale mode. In the later instance, the resulting image is called the "tissue image" and looks similar to grayscale images obtained without contrast injection, showing only a small enhancement in areas of contrast uptake.

It is noted that CEUS can provide superior visualization of tumors, vascularity, and other tissues of interest compared to non-contrast enhanced ultrasound imaging. However, the contrast enhancement after bolus injection is a transient phenomenon, and typically disappears after a few minutes. Such a time limitation of a few minutes is often insufficient time to perform a desired procedure (e.g., such a placing a needle for biopsy or ablation). In other words, for guidance during interventional procedures such as needle placement for biopsy and ablation, the time window of the contrast enhancement is insufficient in comparison to the time required to perform the interventional procedure. A second injection of the contrast agent is possible to prolong the enhancement effect, but this may still be insufficient to complete the desired procedure.

Additional limitations of prior techniques associated with use of a pre-acquired CEUS volume alone include, for example, the position of a subsequent acquired real time ultrasound tissue image during the interventional procedure relative to the pre-acquired CEUS volume is unknown and needs to be estimated, thus being prone to inaccuracy. Furthermore, tissue motion complicates an estimation of target location based upon a pre-acquired CEUS volume.

Accordingly, an improved method and system for overcoming the problems in the art is desired.

In the figures, like reference numerals refer to like elements. In addition, it is to be noted that the figures may not be drawn to scale.

The embodiments of the present disclosure provide a system and method to utilize contrast-enhanced ultrasound imaging (CEUS) for image guidance during interventional procedures. In particular, the embodiments of the present disclosure advantageously enable a method and system for using CEUS to improve targeting accuracy in interventional procedures without having to modify the workflow or switch to a different imaging modality entirely.

The system and method, as disclosed herein, includes a spatial tracking system configured to track the position of an ultrasound probe. Use of the tracking system enables determination of the location of a 3D CEUS volume at the beginning of an interventional procedure. In one embodiment, a 3D tissue volume is also acquired simultaneously with the 3D CEUS volume, as discussed further herein below. Thereafter, during the interventional procedure, spatial tracking of the ultrasound probe enables joint display of a current real time ultrasound tissue image with a corresponding CEUS multi-planar reconstruction (MPR), wherein the corresponding MPR is derived from the initial 3D CEUS volume. Tissue motion between the initial 3D CEUS acquisition and the real time ultrasound tissue imaging is corrected by image-based registration between the real time ultrasound tissue image and the 3D ultrasound tissue volume co-acquired with the initial 3D CEUS volume. The joint display of (i) a corresponding MPR derived from the initial CEUS volume and (ii) real time non-contrast ultrasound tissue image advantageously enables joint visualization of a needle position and target location, and thus enables guidance of the needle into the target for the duration of the interventional procedure, subsequent to expiration of the enhancement effect of the contrast agent.

Figure 1:
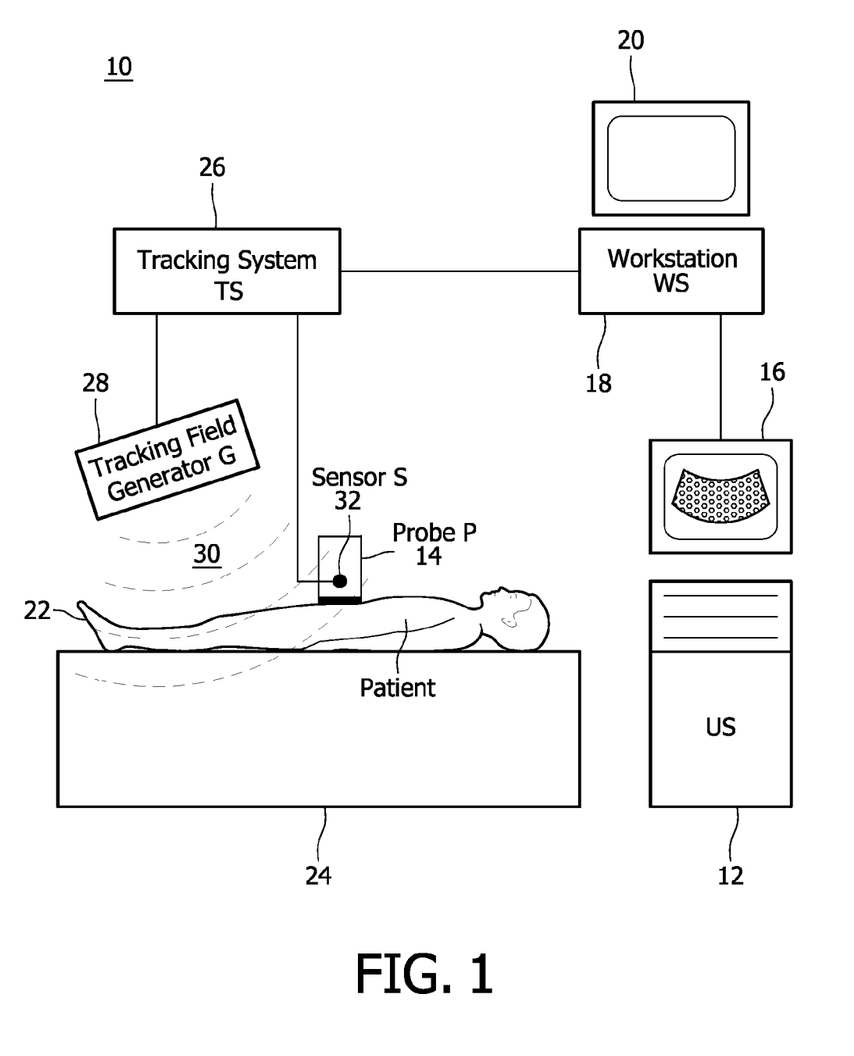
FIG. 1 is a partial block diagram view of a system for implementing a method for interventional navigation using 3D contrast-enhanced ultrasound according to one embodiment of the present disclosure.

Turning now to the drawings, FIG. 1 is a block diagram view of a system 10 for interventional navigation using 3D contrast-enhanced ultrasound according to one embodiment of the present disclosure. System 10 comprises an ultrasound scanner (US) 12 equipped and/or coupled with an ultrasound imaging probe 14. In one embodiment, the ultrasound scanner 12 comprises, for example, an iU22 ultrasound scanner commercially available from Philips Medical Systems. Imaging probe 14 comprises any suitable 3D ultrasound imaging probe. In addition, ultrasound scanner 12 includes a scanner display 16. Furthermore, ultrasound scanner 12 is configured for simultaneous acquisition of contrast and tissue images. Ultrasound scanner 12 is further configured for transferring images in real-time, for example, via data streaming, to workstation 18. For example, transferring images in real-time can be accomplished using an iU22 ultrasound scanner with Digital Navigation Link software. While illustrated as separate from the ultrasound scanner 12, workstation 18 may also be integrated in and part of the ultrasound scanner 12.

Referring still to FIG. 1, workstation 18 includes a workstation display 20. In operation, the ultrasound scanner 12, probe 14, and workstation 18 are used in conjunction with a patient 22 having an anatomy that is subject to a given ultrasound diagnosis and/or a corresponding treatment or medical procedure, wherein the patient 22 is positioned upon a patient table 24. Ultrasound scanner 12 is configured to acquire contrast and tissue ultrasound images, for example, in a "side by side mode" corresponding to an interleaved acquisition of contrast and tissue frames, and sends both acquired images to the workstation 18. Software is executed by workstation 18 to accommodate the workflow as discussed further herein.

The system 10 for interventional navigation using 3D contrast-enhanced ultrasound also includes position tracking according to the embodiments of the present disclosure. System 10 is enhanced by integration with an external position tracking system (TS) 26. The external position tracking system 26 includes a tracking field generator 28 which is configured for producing a tracking field, generally designated by reference numeral 30. A sensor 32 is coupled to the ultrasound probe 14, wherein responsive to the sensor being located within a range of sensing field 30, the sensor's position and orientation can be tracked by the tracking system 26. In one embodiment, workstation 18 is coupled to tracking system 26 and configured to communicate tracking information and/or provide tracking instructions between workstation 18 and tracking system 26 according to the requirements of a given interventional navigation or implementation. Tracking system 26 can comprise any suitable tracking system, for example, such as the electro-magnetic "Aurora" system by Northern Digital Inc., of Waterloo, Canada. In another embodiment, tracking system 26 includes an optical tracking system, in which tracking field generator 28 comprises, for example, a camera, for optically tracking the ultrasound probe 14 within the tracking field 30 corresponding to an optical field of view. Such an optical tracking system may comprise, for example, a "Polaris" system by Northern Digital Inc., of Waterloo, Canada.

In system 10 of FIG. 1, the external position tracking system (TS) 26 is set up next to or proximate the patient 22. A 6 degree-of-freedom (6 DoF) position sensor (S) 32 is coupled to the ultrasound probe 14, and the tracking field generator 28 is positioned such that the probe position can be tracked within tracking field 30.

Workstation 18 also includes software contained on computer readable medium and loaded in a memory thereof, wherein the software includes instructions executable by a processor of the workstation to (i) acquire and store at least one 3D CEUS volume, together with the volume's tracking system coordinates provided by the sensor 32, and (ii) acquire and process tracking sensor coordinates in real time, and using the real-time tracking sensor coordinates for computing and displaying multi-planar reconstructions (MPRs) of the at least one acquired and stored 3D CEUS volume, such that the corresponding MPR shows the same tissues as the latest acquired real time tissue image.

In one embodiment, the ultrasound scanner 12 is configured to acquire and transmit a CEUS image/volume and a tissue image/volume simultaneously. In such an embodiment, the software of workstation 18 further includes instructions executable by the processor of the workstation 18 to (iii) acquire and store simultaneously acquired 3D CEUS volumes and 3D tissue volumes, together with the corresponding volumes' tracking system coordinates provided by the sensor 32; and (iv) acquire and process tracking sensor coordinates in real time, and use the real time tracking sensor coordinates for image-based registration of the non-contrast real time tissue image with the 3D tissue volume acquired simultaneously with the 3D CEUS volume, wherein a resulting registration transformation is used for computing and displaying MPRs of the initial acquired and stored 3D CEUS volume, such that the CEUS MPR shows the same tissues as the latest acquired real time tissue image.

In one embodiment, the system and method comprise using an ultrasound scanner 12 capable of acquiring real time 3D images in contrast and tissue mode, and capable of streaming (i.e., transferring in real time) the image data to the workstation 18 (or other system, for example, via a suitable communication network). In conjunction with this embodiment, the method assumes that a patient is able to follow breathing commands and is further able to produce reproducible breath holds. Furthermore, software running on workstation 18 is configured to communicate with various hardware (e.g., tracking system, ultrasound scanner, etc.) using real time electronic data transfer.

In one example of workflow, a patient 22 being presented for an ultrasound-guided needle ablation is positioned on an examination table 24. Position sensor 32 is attached to the ultrasound probe 14. The transmitter/receiver 28 of tracking system 26 is be positioned close to the patient 22 such that the ultrasound probe 14 with attached position sensor 32 is in the field of view 30 of the transmitter/receiver 28 during the necessary ultrasound imaging for the procedure. The ultrasound scanner 12 is initially configured or set to contrast imaging mode, and an intra-venous bolus injection of contrast agent is administered to the patient 22. Upon the contrast enhancement becoming visible in the ultrasound image displayed on display 16, a three-dimensional (3D) CEUS scan covering the tumor or area of interest is then acquired. The 3D CEUS volume and corresponding probe position data is transferred to the navigation workstation 18. For subsequent imaging after the contrast enhancement has disappeared, the real time 2D or 3D ultrasound tissue images and corresponding probe position data are continuously transferred (i.e., streamed) to the workstation 18. Based on the current probe position, the location of the current ultrasound tissue image relative to the initially acquired 3D CEUS image (also referred to as a pre-acquired 3D CEUS image) is calculated. On the workstation display 20, the current real-time ultrasound tissue image is displayed jointly with the corresponding multi-planar reconstruction (MPR) (or other visualization) of the CEUS image. This allows localizing the needle in the real time tissue image, and localizing the tumor in the CEUS image, and thus enabling guidance of the needle into the tumor, wherein the tumor may not be visible in the real time tissue image alone.

Figure 2:
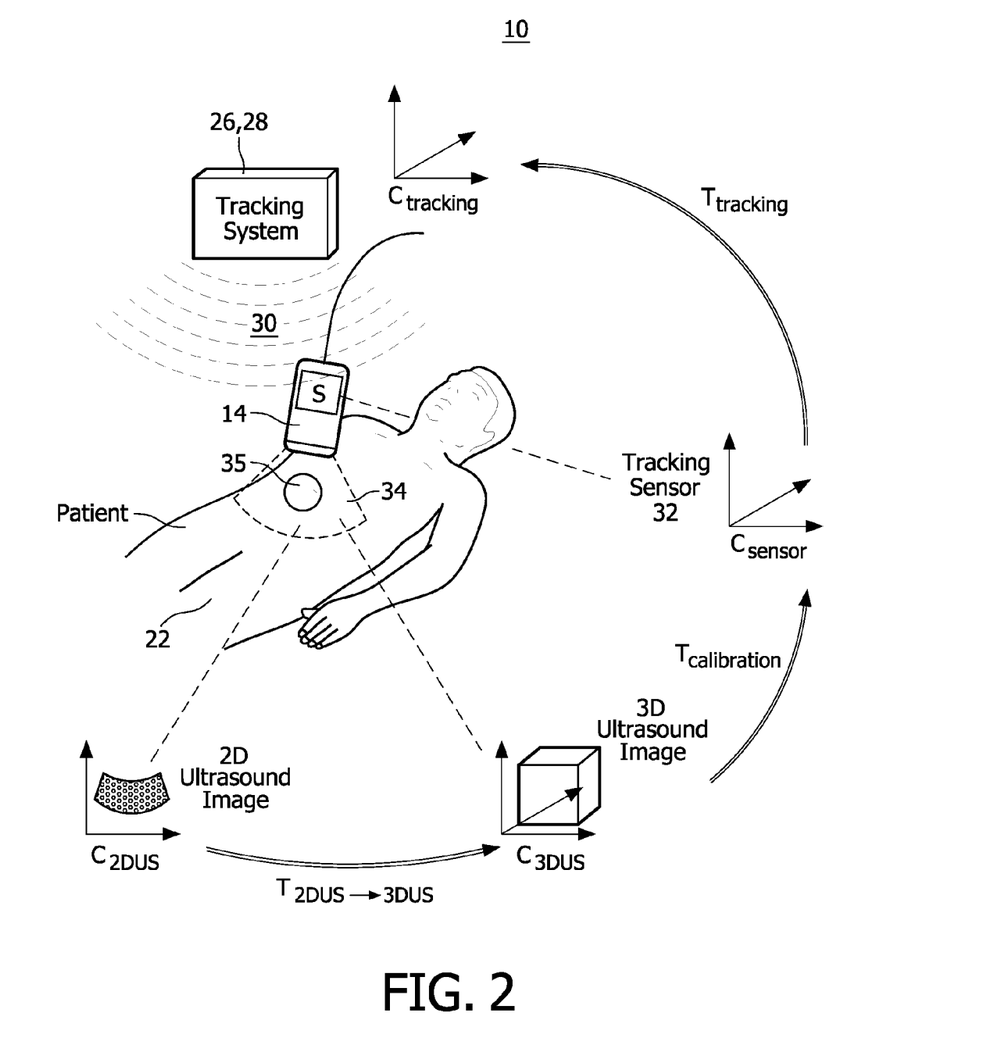
FIG. 2 is a partial block diagram view illustrating transformations between various coordinate systems relevant to the method for interventional navigation using 3D CEUS, according to embodiments of the present disclosure.

FIG. 2 is a partial block diagram view illustrating transformations between various coordinate systems relevant to the system for interventional navigation using 3D contrast-enhanced ultrasound of FIG. 1, according to embodiments of the present disclosure. In particular, FIG. 2 is an illustration of transformations between the coordinate systems of a 2D ultrasound image, a 3D ultrasound image, the tracking sensor attached to the ultrasound probe, and the tracking system. In one embodiment, FIG. 2 illustrates the relationship of transformations between the 6 DoF position sensor, the tracking system, and the corresponding ultrasound frame.

The transformation $T_{tracking}$ describes a current position and orientation (otherwise referred to as a "pose") of the tracking sensor 14 relative to the tracking system (26,28). In other words, the transformation $T_{tracking}$ describes the relationship between the coordinate system of tracking system $C_{tracking}$ and the coordinate system of the tracking sensor $C_{sensor}$. The transformation $T_{tracking}$ is provided by the tracking system and is acquired by the workstation 18, for example, continuously in real time or as required for a given implementation of the interventional procedure according to the embodiments of the present disclosure. The transformation $T_{calibration}$ describes the relationship between the coordinate system $C_{3DUS}$ of the 3D ultrasound image (i.e., voxel coordinates) and the coordinate system $C_{sensor}$ of the tracking sensor 38 attached to the probe 14. The transformation $T_{calibration}$ is determined in a one-time calibration procedure and remains fixed for a given tracking sensor 32 rigidly attached to the ultrasound probe 14, subject to being re-calibrated upon replacement of and/or change in the sensor and/or probe. Lastly, the transformation $T_{2DUS \rightarrow 3DUS}$ describes the relationship between the coordinate system $C_{2DUS}$ of a 2D ultrasound image and the coordinate system $C_{3DUS}$ of the 3D ultrasound image (i.e., voxel coordinates). That is, the transformation between coordinate systems for tracked 2D and 3D ultrasound image acquisition is given by $T_{2DUS \rightarrow 3DUS}$. In summary, the transformation $T_{2DUS \rightarrow 3DUS}$ transforms 2D image pixel coordinates to 3D image voxel coordinates, $T_{calibration}$ transforms 3D image voxel coordinates into sensor coordinates, and $T_{tracking}$ transforms sensor coordinates into tracking system coordinates. Note that $T_{tracking}$ is the real time pose information of the sensor 32 provided by the tracking system (26,28).

According to one embodiment, CEUS image acquisition is a follows. After contrast injection, the navigation software on the workstation requests the sonographer to find a probe position that visualizes the tumor target in 3D CEUS mode. All 3D images from the scanner and all position data from the sensor are continuously streamed to the workstation. When an appropriate image has been acquired and confirmed on the workstation, the image will be stored on the workstation along with the corresponding probe position $T_{tracking, 3DCEUS}$ given by the tracking sensor. The reference coordinate system assigned to the 3D CEUS volume is that of the tracking system, which is immobile throughout the procedure. Using the illustration in FIG. 2, the transformation from 3D CEUS voxel coordinates to tracking system coordinates is given by:

$$T_{3DCEUS} = T_{calibration} \cdot T_{tracking, 3DCEUS}$$

In addition, the embodiments of the present disclosure provide image guidance as follows. After 3D CEUS acquisition, the ultrasound scanner is switched to 2D imaging mode for image guidance. The transformation $T_{2DUS \rightarrow 3DUS}$ between the 2D image coordinates and 3D image coordinates is known based on the imaging algorithms on the ultrasound scanner. Thus, using the current tracking data $T_{tracking}$ from the tracking sensor, the position of the current 2D ultrasound tissue image within the CEUS reference image acquired with $T_{tracking, 3DCEUS}$, can be determined using the transformation:

$$T_{2DUS \rightarrow 3DCEUS} = T_{2DUS \rightarrow 3DUS} \cdot T_{calibration} \cdot T_{tracking} \cdot (T_{3DCEUS})^{-1}$$
$$= T_{2DUS \rightarrow 3DUS} \cdot T_{calibration} \cdot T_{tracking} \cdot$$
$$(T_{tracking, 3DCEUS})^{-1} \cdot (T_{calibration})^{-1}$$

Figure 3:
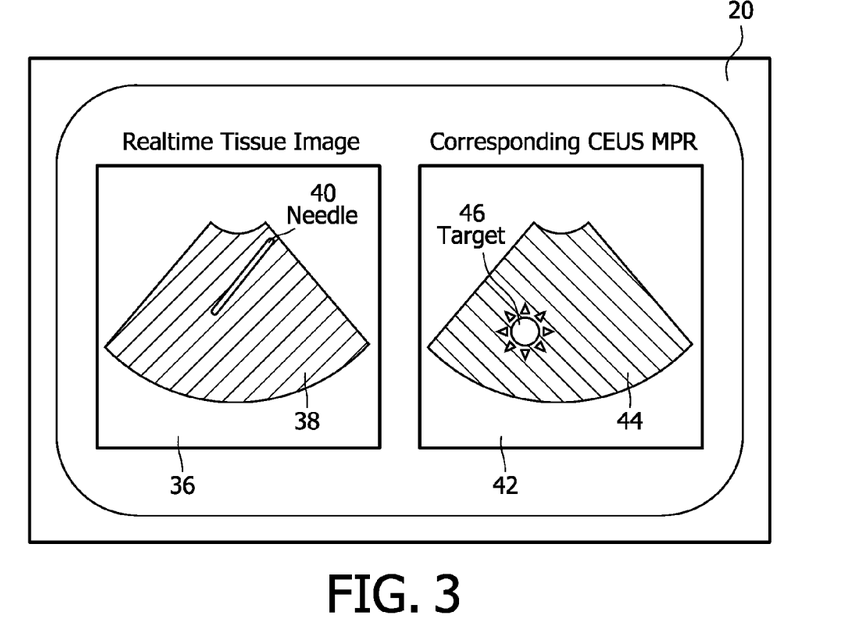
FIG. 3 is a display view illustrating the side-by-side display of real time tissue and corresponding CEUS multi-planar reconstruction (MPR) image views according to one embodiment of the present disclosure.
Figure 4:
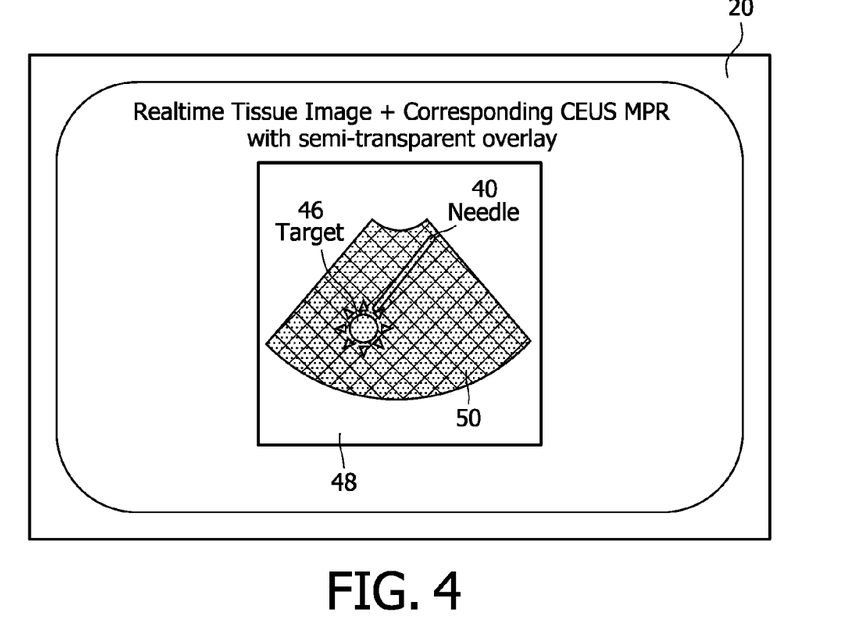
FIG. 4 is a display view illustrating the display of real time tissue and corresponding CEUS MPR images views with semi-transparent overlay according to another embodiment of the present disclosure.

The workstation will use this relationship to extract—in real time—the MPR from the 3D CEUS image that corresponds to the current pose of the 2D tissue image. In one embodiment, both images are displayed side-by-side, or in another embodiment, displayed using semi-transparent overlay with user-determined transparency, on the workstation display 20. FIG. 3 in an illustrative view of the side-by-side display 36 of real time tissue image 38, showing an inserted needle 40, and display 42 of the corresponding MPR 44 from the pre-acquired CEUS volume, showing the target 46 highlighted by the contrast enhancement. FIG. 4 is an illustrative view of a semi-transparent overlay 48 of the same tissue and contrast image, as indicated in FIG. 4 by reference numeral 50.

According to another embodiment, the method includes acquisition of multiple 3D CEUS volumes. That is, during the 3D CEUS volume acquisition, rather than storing on the workstation 18 only a single volume showing the contrast-enhance tissue of interest, a time series of volumes and their corresponding position information are also stored. The method can then ascertain the dynamics of contrast uptake (e.g., in-flow and out-flow), which are also diagnostically valuable indicators. The method further comprises (a) co-displaying not just a single CEUS MPR with the real time tissue image, but co-displaying multiple MPRs of the entire time-series as a "movie". In addition, the method also includes (b) processing the time-series data to create a volumetric map of diagnostically relevant parameters, such as the in-flow time constant, and then co-displaying an MPR of this parameter MAP with the real time tissue image during the interventional procedure.

In another embodiment, the method includes using alternate target visualization. That is, rather than co-displaying or over-laying an MPR of the 3D CEUS volume with the tissue image, a target volume-of-interest (VOI) is segmented from the 3D CEUS volume after CEUS acquisition. Such a target VOI includes, for example, a sphere covering the area of strongest tissue enhancement in the 3D CEUS volume. In this embodiment, during the interventional procedure, only the appropriate cross-section of the VOI, as determined by the current tracking position, would be superimposed on the real time tissue image.

In another embodiment, the method includes using real time 3D imaging during guidance. That is, instead of using 2D imaging for guidance, the method uses real time 3D imaging. In this case, rather than generating MPRs, other means of visualization are used, such as maximum intensity projections (MIPs). The MIP projections can be computed using the same set of transformations as described in the embodiments herein above.

In yet another embodiment, the method uses non-real time 3D CEUS acquisition. In this embodiment, for example, if real time 3D CEUS is not available, the reference CEUS volume can also be generated by tracking a 2D ultrasound probe, streaming to the workstation all 2D image frames and corresponding tracking data, obtaining a "sweep" over the target area after contrast injection, and reconstructing the 3D CEUS volume based on the acquired 2D images and tracking data.

In a further embodiment, the method includes use of image-based registration for motion correction. In this embodiment, the above described joint display of real time tissue image and corresponding 3D CEUS MPR is only accurate if the patient, or the organ being imaged, does not move between acquisition of the 3D CEUS volume and of the real time tissue image. To enhance the accuracy in the presence of tissue motion, the method according to the embodiments of the present invention further includes, for example, one of the following motion correction methods. A first motion correction method includes simultaneous acquisition of the 3D CEUS image with a 3D tissue image. This motion correction method makes use of a simultaneous dual-mode acquisition and visualization, for example, as is available in real time 2D on modern scanners such as Philips iU22, and which enables non-real time simultaneous 3D acquisition as described above. A second motion correction method includes an image-based registration of a current 2D tissue image (or the last N 2D tissue images, with N is small, e.g. <10) with the 3D tissue image acquired simultaneously with the 3D CEUS image. The tracking coordinates associated with the 2D images serve as a starting position for the registration (i.e. assuming no organ motion). The registration itself can utilize various optimizers and similarity measures, such as the Gauss-Newton optimizer and sum-of-squared-differences similarity measure. The result of the registration is the transformation $T_{2DUS \to 3Dtissue}$. Since the 3D CEUS and tissue images were acquired simultaneously, their coordinate systems are identical, and the same transformation can be used to transform current 2D coordinates into 3D CEUS coordinates.

As discussed herein, the system and method according to the embodiments of the present disclosure use a spatial tracking system to track the position of an ultrasound probe and for image guidance in interventional procedures during contrast-enhanced ultrasound imaging (CEUS). At the beginning of an interventional procedure, a three-dimensional (3D) CEUS volume is acquired simultaneously with a regular 3D ultrasound tissue image. During the procedure, spatial tracking of the ultrasound probe enables joint display of the current real time ultrasound tissue image with the corresponding multi-planar reconstruction (MPR) from the 3D CEUS volume acquired at the beginning of the procedure (also referred to herein as the pre-acquired 3D CEUS volume). Tissue motion between 3D CEUS acquisition obtained at the beginning of the procedure and real time imaging obtained subsequent or after the beginning of the procedure is corrected by image-based registration between the real time 3D tissue image and a 3D tissue image co-acquired with the 3D CEUS at the beginning of the procedure. The joint display of pre-acquired CEUS, and more particularly, a multi-planar reconstruction (MPR) of the pre-acquired CEUS, wherein the MPR corresponds to a given tissue image in real time, and real time non-contrast ultrasound enables joint visualization of needle position and target location, and thus enables guidance of the needle into the target. As previously discussed, CEUS can provide superior visualization of tumors, vascularity, and other tissues of interest compared to non-contrast enhanced ultrasound imaging. By itself, contrast enhancement after bolus injection is a transient phenomenon and typically disappears after a few minutes. For guidance during interventional procedures such as needle placement for biopsy and ablation, the time window of the transient phenomenon of contrast enhancement alone is insufficient. However, the embodiments of the present disclosure advantageously provide a system and method that overcomes this limitation.

Accordingly, by now it will be appreciated that a method for interventional navigation using 3D contrast-enhanced ultrasound (CEUS) imaging as disclosed herein comprises: acquiring a reference 3D CEUS volume and tracking information for a desired portion of an anatomy that is subject to an interventional procedure with an instrument, wherein the acquiring takes place during a useful lifetime of a contrast enhancement agent administered to the desired portion of the anatomy; acquiring real-time tracked tissue images during the interventional procedure; generating at least one corresponding contrast-enhanced ultrasound image multiplanar reconstruction (CEUS MPR) for at least one of the acquired real-time tracked tissue images during the interventional procedure as a function of the reference 3D CEUS volume and tracking information; displaying at least one of the acquired real-time tracked tissue images, wherein the displayed real-time tracked tissue image includes at least an image of the instrument within the desired portion of the anatomy; and displaying the at least one corresponding contrast-enhanced ultrasound image multiplanar reconstruction (CEUS MPR) that corresponds to the displayed real-time tracked tissue image, wherein the CEUS MPR image includes a contrast enhanced MPR image obtained from the reference 3D CEUS volume and includes a target volume of interest, thereby providing a concurrent display of contrast enhanced image information and tissue image information useful for the interventional navigation at least subsequent to the expiration of the contrast enhancement useful lifetime.

According to another embodiment, acquisition of the reference 3D CEUS volume includes concurrent acquisition of at least one tracked 3D ultrasound contrast image and tissue image pair. In addition, the at least one tracked 3D ultrasound contrast and tissue image pair comprise an initial ultrasound contrast image and a corresponding initial tissue image captured substantially concurrently and automatically registered to one another.

In another embodiment, the interventional procedure includes a first portion thereof that occurs prior to expiration of the contrast enhancement useful lifetime and a second portion thereof that occurs subsequent expiration of the contrast enhancement useful lifetime. In a further embodiment, the at least one corresponding contrast-enhanced ultrasound image multiplanar reconstruction is spatially registered with a corresponding one of the acquired real-time tracked tissue images. In another embodiment, the real-time tracked tissue image and the corresponding CEUS MPR are displayed adjacent to one another. In yet another embodiment, the real-time tracked tissue image and the corresponding CEUS MPR reference image are displayed together on a single display. In the latter instance, the real-time tracked tissue image and the corresponding CEUS MPR can further be displayed in an overlaying arrangement such that one image overlays the other image. Still further, the overlaying arrangement can comprise one image being semi-transparent with respect to the other image.

According to another embodiment, instead of generating at least one corresponding contrast-enhanced ultrasound image multiplanar reconstruction (CEUS MPR) for at least one of the acquired real-time tracked tissue images during the interventional procedure, and instead of displaying the acquired real-time tracked tissue images, the method comprises: generating a maximum intensity projection (MIP) as a function of the at least one pair of acquired tracked 3D real-time ultrasound contrast and tissue images; displaying a maximum intensity projection (MIP) of at least one of the acquired real-time tracked 3D tissue images, wherein the displayed real-time tracked tissue image MIP includes at least an image of the instrument within the desired portion of the anatomy; and displaying the at least one corresponding contrast-enhanced ultrasound image maximum intensity projection (CEUS MIP) that corresponds to the displayed MIP of the at least one acquired real-time tracked 3D tissue image, wherein the CEUS MIP image includes a contrast enhanced MIP image from a target volume of interest, thereby providing a concurrent display useful for the interventional navigation at least subsequent to the expiration of the contrast enhancement useful lifetime.

In another embodiment, in the absence of real-time 3D ultrasound, the reference 3D CEUS volume is acquired by tracking a 2D ultrasound probe, acquiring a series of 2D contrast and tissue image frames and corresponding tracking data while sweeping the tracked 2D ultrasound probe over the desired portion of the anatomy after contrast enhancement agent administration, streaming the acquired series of 2D contrast and tissue images and corresponding tracking data to a workstation, and reconstructing the reference 3D CEUS volume at the workstation based upon the acquired 2D contrast and tissue images and corresponding tracking data.

In yet another embodiment, acquiring the reference 3D CEUS volume includes using a spatial tracking system configured to track a position of an ultrasound probe used in acquiring the reference 3D CEUS volume, wherein the tracking system enables determination of a location and orientation of the reference 3D CEUS volume; and wherein the tracking system is further configured to track the acquired tissue images during the interventional procedure. The method further comprises: correcting for tissue motion within the desired portion of the anatomy which may occur between (i) a time of the acquisition of the reference 3D CEUS volume, and (ii) a time of the acquisition of the at least one real-time tracked tissue image. Still further, correcting tissue motion includes using an image-based registration between (a) the real-time tracked 3D tissue image and (b) the ultrasound tissue image of the tracked 3D ultrasound contrast and tissue image pair.

According to another embodiment, acquiring the reference 3D CEUS volume and tracking information includes acquiring a time series of 3D CEUS volumes and corresponding tracking information, and wherein generating the at least one corresponding CEUS MPR image includes generating a time series of CEUS MPR images, and wherein displaying the acquired real-time tracked tissue images and displaying the at least one corresponding CEUS MPR images comprises co-displaying the CEUS MPR images with the real-time tissue images as time-series data. The method further comprises processing the time-series data to create a volumetric map of diagnostically relevant parameters, and co-displaying the volumetric map with (i) the CEUS MPR images and (ii) the real-time tissue images. In addition, the diagnostically relevant parameters can include at least an in-flow time constant of the contrast agent.

In yet another embodiment, the method further comprises segmenting the target volume of interest from the reference 3D CEUS volume, wherein the target volume of interest comprises an areas of strongest tissue enhancement; and displaying a corresponding cross-section segment of the target volume of interest, instead of displaying the at least one corresponding contrast-enhanced ultrasound image multiplanar reconstruction (CEUS MPR), that corresponds to the displayed real-time tracked tissue image, and superimposing the corresponding cross-section segment of the target volume of interest on the displayed real-time tracked tissue image.

According to a further embodiment, a method for interventional navigation using 3D contrast-enhanced ultrasound (CEUS) imaging comprises: acquiring a reference 3D CEUS volume and tracking information for a desired portion of an anatomy that is subject to an interventional procedure with an instrument, wherein the acquiring takes place during a useful lifetime of a contrast enhancement agent administered to the desired portion of the anatomy, wherein acquisition of the reference 3D CEUS volume includes concurrent acquisition of at least one tracked 3D ultrasound contrast image and tissue image pair; acquiring real-time tracked tissue images during the interventional procedure; generating at least one corresponding contrast-enhanced ultrasound image multiplanar reconstruction (CEUS MPR) for at least one of the acquired real-time tracked tissue images during the interventional procedure as a function of the reference 3D CEUS volume and tracking information, wherein the at least one corresponding contrast-enhanced ultrasound image multiplanar reconstruction is spatially registered with a corresponding one of the acquired real-time tracked tissue images; displaying the acquired real-time tracked tissue images, wherein the displayed real-time tracked tissue image includes at least an image of the instrument within the desired portion of the anatomy; and displaying the at least one corresponding contrast-enhanced ultrasound image multiplanar reconstruction (CEUS MPR) that corresponds to the displayed real-time tracked tissue image, wherein the CEUS MPR image includes a contrast enhanced MPR image obtained from the reference 3D CEUS volume and includes a target volume of interest, thereby providing a concurrent display of contrast enhanced image information and tissue image information useful for the interventional navigation at least subsequent to the expiration of the contrast enhancement useful lifetime.

In yet another embodiment, a system for interventional navigation using 3D contrast-enhanced ultrasound (CEUS) imaging comprises: an ultrasound imaging device configured to (i) acquire a reference 3D CEUS volume and tracking information for a desired portion of an anatomy that is subject to an interventional procedure with an instrument, wherein the ultrasound imaging device is further configured to acquire the reference 3D CEUS volume and tracking information during a useful lifetime of a contrast enhancement agent administered to the desired portion of the anatomy, (ii) acquire real-time tracked tissue images during the interventional procedure, and (iii) generate at least one corresponding contrast-enhanced ultrasound image multiplanar reconstruction (CEUS MPR) for at least one of the acquired real-time tracked tissue images during the interventional procedure as a function of the reference 3D CEUS volume and tracking information; and a display coupled to the ultrasound imaging device and configured to display (i) the acquired real-time tracked tissue images, wherein the displayed real-time tracked tissue images include at least an image of the instrument within the desired portion of the anatomy, and (ii) at least one corresponding contrast-enhanced ultrasound image multiplanar reconstruction (CEUS MPR) that corresponds to the displayed real-time tracked tissue image, wherein the CEUS MPR image includes a contrast enhanced MPR image obtained from the reference 3D CEUS volume and includes a target volume of interest, thereby providing a concurrent display of contrast enhanced image information and tissue image information useful for the interventional navigation at least subsequent to the expiration of the contrast enhancement useful lifetime.

As discussed herein, the embodiments of the present disclosure can be applied in ultrasound-based image guidance of diagnostic and therapeutic medical procedures. For example, the embodiments of the present disclosure can improve needle guidance for biopsy and ablation procedures. In addition, the embodiments of the present disclosure advantageously overcome limitations and disadvantages in current ultrasound-based procedure guidance, such as, limited visualization or no visualization of some tumors/targets; poor accuracy in execution of the procedure if target location is estimated based on a pre-acquired modality (other than pre-acquired CEUS as disclosed with respect to the embodiments of the present disclosure); and brief duration of contrast enhancement in CEUS imaging which is insufficient for execution of a given interventional procedure.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A method for interventional navigation using 3D contrast-enhanced ultrasound (CEUS) imaging during an interventional procedure with an instrument in a desired portion of an anatomy, the method comprising the acts of:
   administering a contrast enhancement agent to a tracked tissue including the desired portion of the anatomy;
   during the interventional procedure, acquiring a reference 3D CEUS volume and tracking information for the desired portion within a useful lifetime of the contrast enhancement agent and acquiring real-time images of the tracked tissue subsequent to expiration of the useful lifetime of the contrast enhancement, wherein the acquiring of the reference 3D CEUS volume includes concurrent acquisition within the useful lifetime of the contrast enhancement agent of a pair of images of the tracked tissue including at least one 3D ultrasound contrast image acquired in 3D CEUS mode and corresponding tissue image of the tracked tissue acquired in grayscale mode, wherein the at least one 3D ultrasound contrast image shows enhancement in areas of uptake of the contrast enhancement agent, and wherein the tissue image shows reduced enhancement in the areas of uptake of the contrast enhancement agent;
   generating a 3D CEUS multiplanar reconstruction (MPR) for at least one of the acquired real-time images as a function of the reference 3D CEUS volume and the tracking information; and
   displaying the acquired real-time images showing the instrument within the desired portion and the corresponding 3D CEUS MPR for the interventional navigation.

2. The method of claim 1, wherein the pair comprises at least an initial 3D CEUS image and a corresponding initial real-time image of the tracked tissue captured concurrently and automatically registered to one another.

3. The method of claim 1, wherein the interventional procedure includes a first portion that occurs prior to the expiration of the useful lifetime of the contrast enhancement and a second portion that occurs subsequent to the expiration of the useful lifetime of the contrast enhancement.

4. The method of claim 1, wherein the 3D CEUS MPRs are spatially registered with a corresponding real-time images.

5. The method of claim 1, wherein the real-time images and the corresponding 3D CEUS MPRs are displayed adjacent to one another.

6. The method of claim 1, wherein the real-time image and the corresponding 3D CEUS MPR are displayed together on a single display.

7. The method of claim 6, wherein the real-time image and the corresponding 3D CEUS MPRs are displayed in an overlaying arrangement such that one overlays the other.

8. The method of claim 7, wherein in the overlaying arrangement one of the real-time image and the corresponding 3D CEUS MPR is semi-transparent with respect to the other.

9. The method of claim 1, wherein the acquiring act comprises acts of:
   tracking a 2D ultrasound probe;
   sweeping the tracked 2D ultrasound probe over the desired for acquiring a series of 2D contrast and tissue images and corresponding tracking data;
   streaming the acquired series of 2D contrast and tissue images and corresponding tracking data to a workstation; and
   reconstructing the reference 3D CEUS volume at the workstation based upon the acquired series of 2D contrast and tissue images and corresponding tracking data.

10. The method of claim 1, wherein the acquiring act comprises the act of tracking a position of an ultrasound probe used in acquiring the reference 3D CEUS volume using a spatial tracking system to determine a location and orientation of the reference 3D CEUS volume and to track the acquired tissue images during the interventional procedure.

11. The method of claim 10, further comprising the act of correcting for motion of tissue within the desired portion of the anatomy occurring between a time of acquisition of the reference 3D CEUS volume and a time of acquisition of the at least one real-time image.

12. The method of claim 11, wherein the correcting act includes using an image-based registration between a pair including the real-time image and the 3D CEUS volume.

13. The method of claim 1, wherein the reference 3D CEUS volume comprises a time series of 3D CEUS volumes, wherein the 3D CEUS MPR comprises a time series of 3D CEUS MPRs, and wherein the displaying act further comprises co-displaying the 3D CEUS MPRs with the real-time images as time-series data.

14. The method of claim 13, further comprising the act of: processing the time-series data to create a volumetric map of diagnostically relevant parameters, and co-displaying the volumetric map with the 3D CEUS MPRs and the real-time images.

15. The method of claim 14, wherein the diagnostically relevant parameters include at least an in-flow time constant of the contrast agent.

16. The method of claim 1, further comprising the acts of:
segmenting from the reference 3D CEUS volume the desired portion having areas of strongest tissue enhancement;
displaying a cross-section segment of the desired portion, instead of the 3D CEUS MPRs that corresponds to the displayed real-time tracked tissue image; and
superimposing the cross-section segment on the displayed real-time image.

17. A method for interventional navigation using 3D contrast-enhanced ultrasound (CEUS) imaging during an interventional procedure with an instrument, the method comprising the acts of:
administering a contrast enhancement agent to a tracked tissue including a desired portion of the anatomy;
during a useful lifetime of the contrast enhancement agent, acquiring a reference 3D CEUS volume and tracking information for the desired portion, and real-time images of the tracked tissue, wherein the acquiring of the reference 3D CEUS volume includes concurrent acquisition of a pair of images of the tracked tissue including at least one 3D ultrasound contrast image acquired in 3D CEUS mode and corresponding tissue image of the tracked tissue acquired in grayscale mode, wherein the at least one 3D ultrasound contrast image shows enhancement in areas of uptake of the contrast enhancement agent, and wherein the tissue image shows reduced enhancement in the areas of uptake of the contrast enhancement agent;
generating a 3D CEUS multiplanar reconstruction (MPR) for at least one of the acquired real-time images as a function of the reference 3D CEUS volume and tracking information, the 3D CEUS MPR is spatially registered with a corresponding acquired real-time images;
displaying the acquired real-time images showing the instrument within the desired portion and the corresponding 3D CEUS MPRs for the interventional navigation at least subsequent to the expiration of the useful lifetime of the contrast enhancement.

18. A system for interventional navigation using 3D contrast-enhanced ultrasound (CEUS) imaging during an interventional procedure with an instrument, the system comprising:
an ultrasound imaging device configured to:
administer a contrast enhancement agent to a tracked tissue including a desired portion of the anatomy;
during a useful lifetime of the contrast enhancement agent, acquire a reference 3D CEUS volume and tracking information for the desired portion, and real-time images of the tracked tissue, wherein the acquiring of the reference 3D CEUS volume includes concurrent acquisition of a pair of images of the tracked tissue including at least one 3D ultrasound contrast image acquired in 3D CEUS mode and corresponding tissue image of the tracked tissue acquired in grayscale mode, wherein the at least one 3D ultrasound contrast image shows enhancement in areas of uptake of the contrast enhancement agent, and wherein the tissue image shows reduced enhancement in the areas of uptake of the contrast enhancement agent; and
generate at least one corresponding 3D CEUS multiplanar reconstruction (MPR) for at least one of the acquired real-time images as a function of the reference 3D CEUS volume and the tracking information; and
a display coupled to the ultrasound imaging device and configured to display the acquired real-time images, showing the instrument within the desired portion, and the corresponding 3D CEUS MPRs for the interventional navigation at least subsequent to the expiration of the contrast enhancement.

19. A method for interventional navigation using 3D contrast-enhanced ultrasound (CEUS) imaging during an interventional procedure with an instrument in a desired portion of an anatomy, the method comprising the acts of:
administering a contrast enhancement agent to a tracked tissue including the desired portion of the anatomy;
during the interventional procedure and within a useful lifetime of the contrast enhancement agent, acquiring a reference 3D CEUS volume and tracking information for the desired portion, and real-time images of the tracked tissue, wherein the acquiring of the reference 3D CEUS volume includes concurrent acquisition of a pair of images of the tracked tissue including at least one 3D ultrasound contrast image acquired in 3D CEUS mode and corresponding tissue image of the tracked tissue acquired in grayscale mode, wherein the at least one 3D ultrasound contrast image shows enhancement in areas of uptake of the contrast enhancement agent, and wherein the tissue image shows reduced enhancement in the areas of uptake of the contrast enhancement agent;
generating a maximum intensity projection (MIP) as a function of the acquired 3D CEUS volume and tracking information and real-time images;
displaying the MIP showing the instrument within the desired portion and the corresponding 3D CEUS MIPs for the interventional navigation.

* * * * *